US00PP18340P3

(12) United States Plant Patent
Jamieson

(10) Patent No.: US PP18,340 P3
(45) Date of Patent: Dec. 25, 2007

(54) STRAWBERRY VARIETY NAMED 'WENDY'

(50) Latin Name: *Fragaria xananassa Duchesne*
Varietal Denomination: Wendy

(75) Inventor: Andrew Jamieson, Kentville (CA)

(73) Assignee: Her majesty the Queen in Right of Canada, as Represented by the Minister of Argriculture and Agri-Food, Kentville, Nova Scotia (CA)

( * ) Notice: Subject to any disclaimer, the term of this patent is extended or adjusted under 35 U.S.C. 154(b) by 0 days.

(21) Appl. No.: 11/274,388

(22) Filed: Nov. 15, 2005

(65) Prior Publication Data

US 2006/0236437 P1 Oct. 19, 2006

(51) Int. Cl.
*A01H 5/00* (2006.01)

(52) U.S. Cl. ..... Plt./208
(58) Field of Classification Search ..... Plt./208, Plt./209
See application file for complete search history.

(56) References Cited

U.S. PATENT DOCUMENTS

| | | | | |
|---|---|---|---|---|
| PP6,170 | P | 5/1988 | Meilland | Plt./9 |
| PP13,081 | P2 | 10/2002 | Crandall | Plt./208 |
| PP13,387 | P2 | 12/2002 | Anderson et al. | Plt./286 |
| PP14,617 | P3 | 3/2004 | Luby et al. | Plt./207 |
| PP15,703 | P3 | 3/2005 | Roose et al. | Plt./202 |

OTHER PUBLICATIONS

Jamieson, A.R., et al., "'Evangeline' strawberry," *HortScience,* 2004, 39(7), 1783–1784.

*Primary Examiner*—Kent Bell
*Assistant Examiner*—S. B. McCormick-Ewoldt
(74) *Attorney, Agent, or Firm*—Woodcock Washburn LLP

(57) ABSTRACT

This invention relates to a new and distinct variety of strawberry (*Fragaria xananassa*) named 'Wendy'. The invention is an early season, short-day variety similar to 'Evangeline'. 'Wendy' is distinguished from 'Evangeline' by its flower characteristics, calyx characteristics, fruit size, fruit shape, and insertion of the achenes.

3 Drawing Sheets

CROSS-REFERENCE TO RELATED APPLICATIONS

This application claims priority under 35 U.S.C. § 119 to Plant Breeder's Rights Certificate Application No. 05-4723, filed in Canada on Apr. 18, 2005, the disclosure of which is incorporated herein by reference in its entirety.

Latin name of the genus and species of the plant claimed: *Fragaria xananassa* Duchesne.

Variety denomination: The new plant has the varietal denomination 'Wendy'.

BACKGROUND OF THE INVENTION

The present invention includes a new and distinct cultivar of *Fragaria xananassa* known by the varietal name 'Wendy', originally designated as 'K98-6'. The new variety resulted from a controlled cross in an ongoing breeding program between the strawberry plants 'K96-5' and 'Evangeline'. 'K96-5' is an unpatented variety. 'Evangeline' is a variety developed by Andrew R. Jamieson for which Canadian Plant Breeder's Rights were granted in 1999 (No. 06170). 'Wendy' was discovered in 1998 as a seedling in a controlled breeding plot near Sheffield Mills, Nova Scotia at the Sheffield Farm where it was selected and propagated asexually by stolons. Asexual propagules from this original source have been produced annually in a greenhouse in Kentville, Canada. 'Wendy' has been tested at a research center in Kentville, Canada (starting in 1999) and also at the Agriculture and Agri-Food Canada research centre at Buctouche, New Brunswick, Canada. This propagation and testing has demonstrated that the combination of traits disclosed herein which characterize the new variety are fixed and retained true to type through successive generations of asexual reproduction via stolons.

BRIEF SUMMARY OF THE INVENTION

The present invention relates to a new and distinct variety named 'Wendy'. The variety is botanically identified as *Fragaria xananassa.* The variety is typical of short-day varieties and produces fruit over a four week period in northern temperate climates. The new variety is distinguished from other varieties by a number of characteristics as set forth in Tables 1, 2, and 3. All measurements are mean measurements unless otherwise indicated.

BRIEF DESCRIPTION OF THE DRAWINGS

The accompanying photographs show typical specimens of the new variety including fruit, foliage and flowers, in color as nearly true as it is reasonably possible to make in color illustrations of these characteristics.

DETAILED BOTANICAL DESCRIPTION

Figure 1:
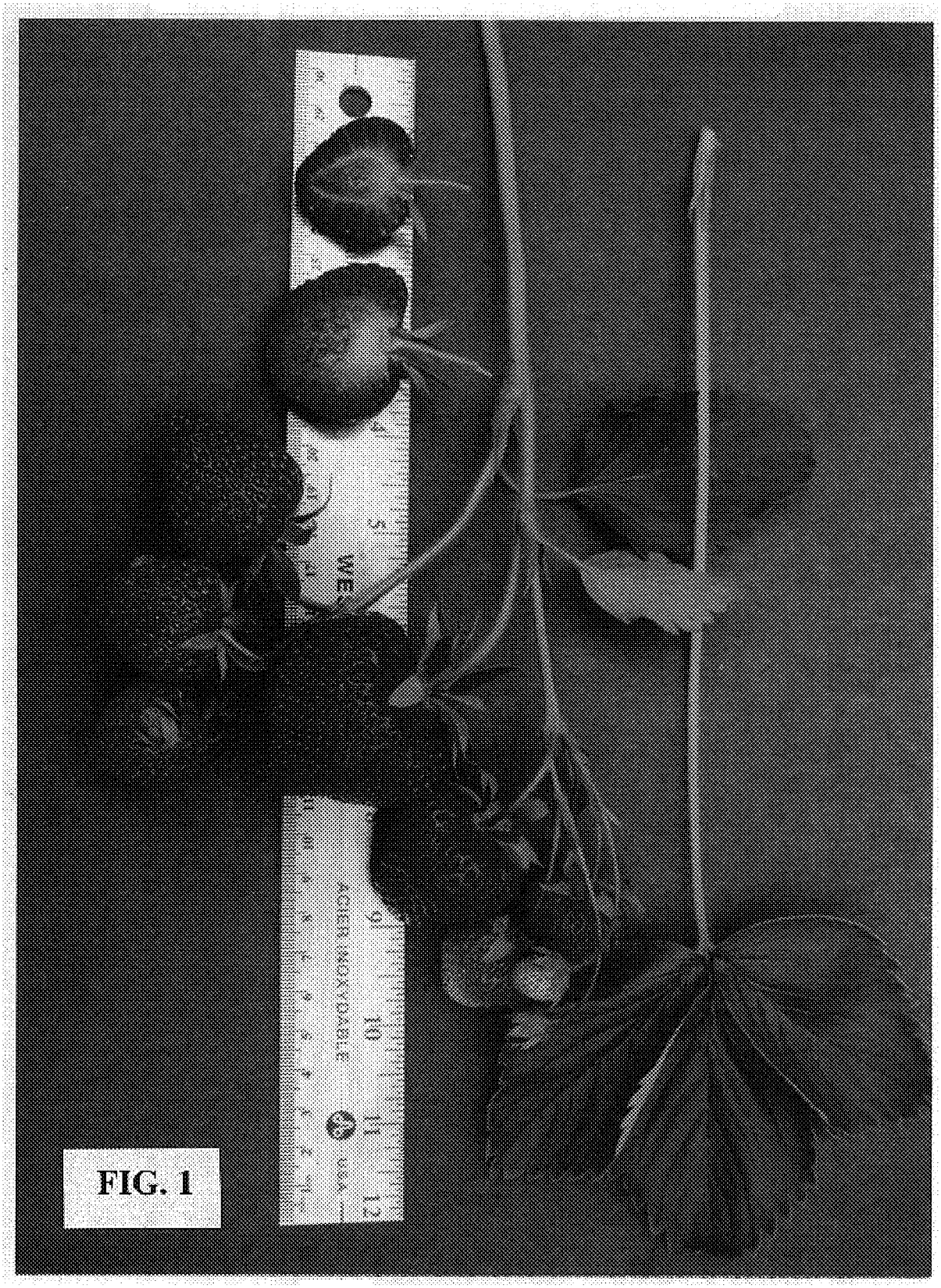
FIG. 1 shows plant parts of the new variety, typical in size, shape, and color.
Figure 2:
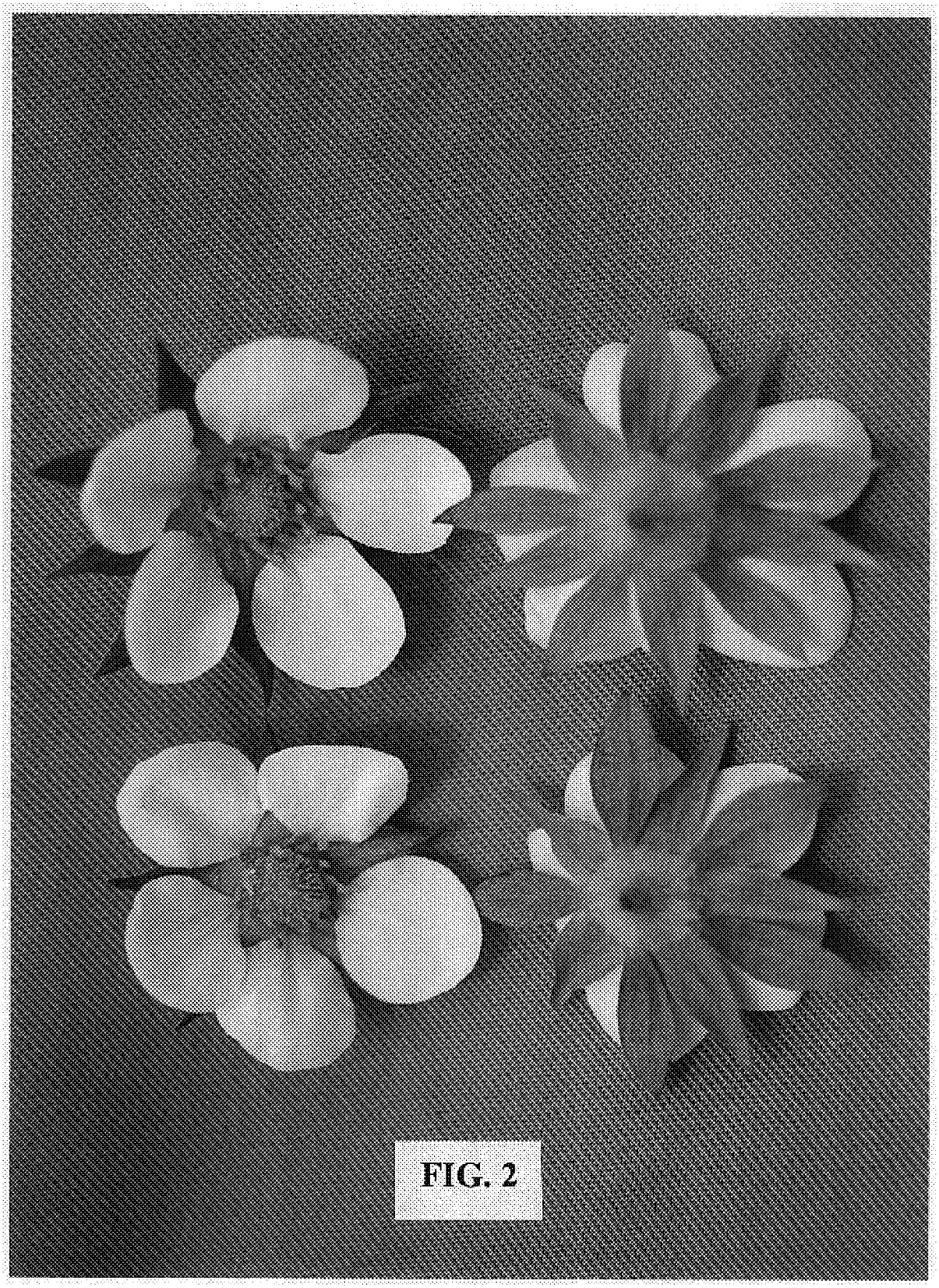
FIG. 2 shows the flowers of the new variety (on the left) compared with Evangeline (on the right).
Figure 3:
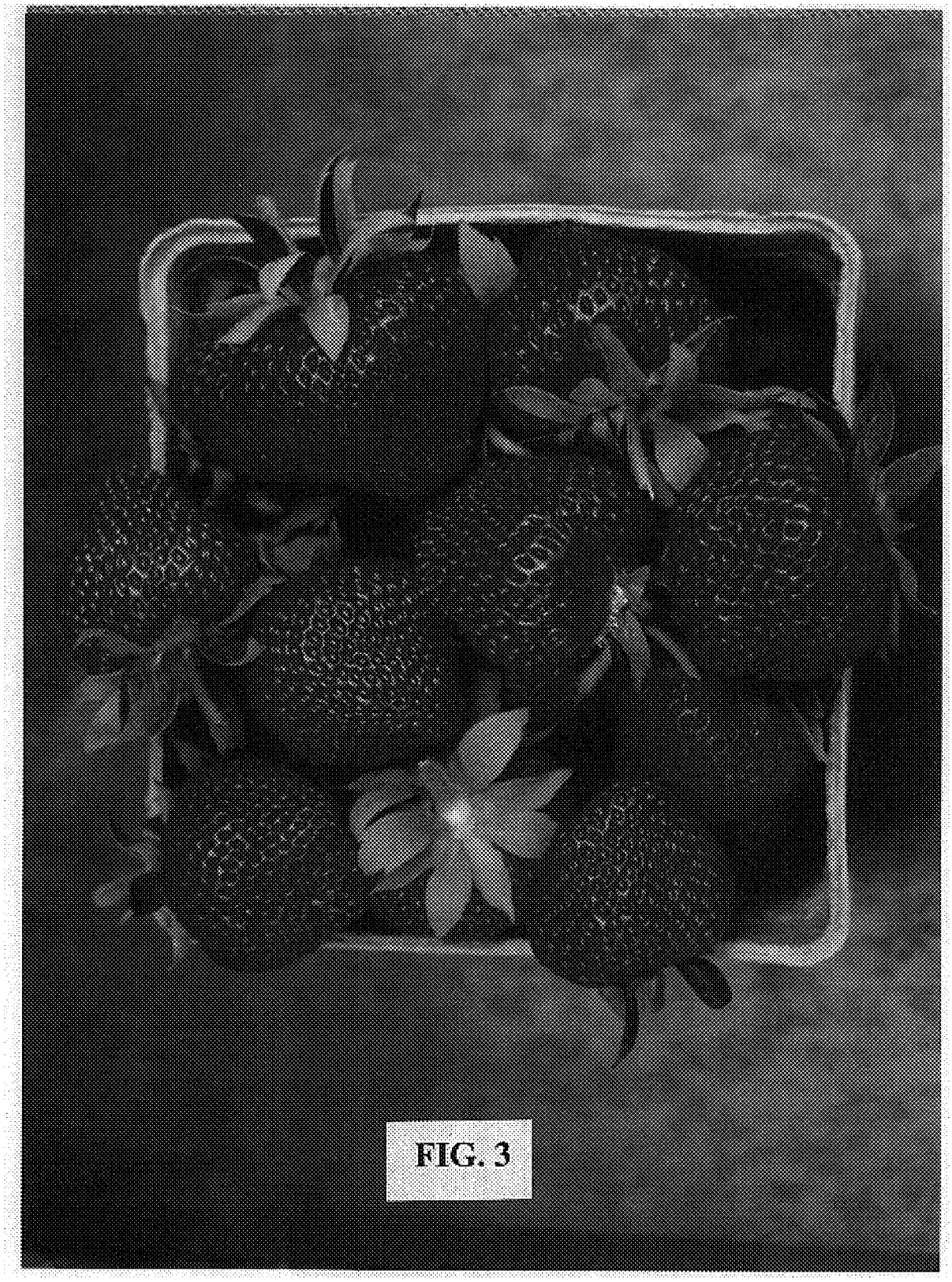
FIG. 3 shows primary fruit of the new variety.

The following detailed botanical description of the new variety, and the similar variety 'Evangeline', is based upon measurements and observations taken of plants and fruit grown in Kentville, Nova Scotia, Canada. Observations were taken from both varieties as grown in a side-by-side field trial in 2002, 2003, 2004 and 2005. This description is in accordance with UPOV terminology. Color designations, color descriptions, and other phenotypical descriptions may deviate from the stated values and description depending upon variation in the environment, seasonal, climatic and cultural conditions, however, it is believed that this description will apply to the 'Wendy' plants grown in similar conditions of soil and climate elsewhere. Colors are described using a standard Royal Horticultural Society Colour Chart. Descriptive information on the new variety is presented in Tables 1 and 2. In the tables, the flowers described are secondary flowers. The fruit described is the secondary fruit of the maiden crop, thirteen or fourteen months after planting. The harvest data in Table 3 is based on a complete harvest of the crop. Principal differences between 'Wendy' and the variety 'Evangeline' are set forth.

The new variety is botanically identified as *Fragaria xananassa* and commercially classified as a short-day strawberry.

Plant and Foliage Characteristics

When propagated in the field nursery, 'Wendy' produces stolons freely; producing similar numbers of daughter plants as 'Evangeline'. Individual plants of 'Wendy' are medium to large. The plants of 'Wendy' are of medium density with globose habit and strong vigor. The plant height of 'Wendy' is 28.2 cm as compared to 'Evangeline' at 24.3 cm. The plant width of 'Wendy' is 38.5 cm as compared to 'Evangeline' at 36.6 cm.

As shown in Table 1, leaf color of 'Wendy' and 'Evangeline' are Green Group 137A on the upper surface and lighter Green Group 137C on the under surface. Leaflets of 'Wendy' and 'Evangeline' are about the same size, shape and convexity, and leaves of both varieties have three leaflets. The leaflet serrations of 'Wendy' are similar in size to 'Evangeline' but for 'Wendy' serrations are more rounded and less pointed than for 'Evangeline' and they have a few more serrations than for 'Evangeline' and, as a result, the portion of the leaf margin without serrations is smaller. The venation of 'Wendy' leaflets is pinnate. Petiole pubescence for 'Wendy' tends to be perpendicular to the petiole, whereas petiole pubescence for 'Evangeline' tends to be oriented upwards, especially near the point of attachment of the leaflets. 'Wendy' produces many stolons. In propagation beds filled with peat-based soil, averaged over three years, 'Wendy' produced 140 daughter plants and 'Evangeline' produced 103 plants. Both varieties have medium to weak density of pubescence on the stolons.

TABLE 1

Foliar characteristics for 'Wendy' and 'Evangeline'.

| | Cultivar | |
|---|---|---|
| Foliar Character | 'Wendy' | 'Evangeline' |
| Leaf color | Green Group | Green Group |
| Upper surface | 137A | 137A |
| Lower Surface | 137C | 137C |
| Central leaflet | | |
| Length (mm) | | |
| Mean | 92.8 | 99.1 |
| Range | 83-99 | 83-114 |

TABLE 1-continued

Foliar characteristics for 'Wendy' and 'Evangeline'.

| | Cultivar | |
|---|---|---|
| Foliar Character | 'Wendy' | 'Evangeline' |
| Width (mm) | | |
| Mean | 78.2 | 79.2 |
| Range | 68-87 | 65-93 |
| Length/width ratio | 1.19 | 1.25 |
| No. leaflets/leaf | 3 | 3 |
| Leaf convexity | cupped | cupped |
| Serrations | | |
| Number | | |
| Mean | 21.0 | 18.2 |
| Range | 19-22 | 16-20 |
| Size | medium | medium |
| Shape | semi-round | semi-pointed |
| Tip serration size | small | small |
| Leaf pubescence | medium | medium |
| Petiole pubescence | | |
| Density | medium | sparse-medium |
| Direction | perpendicular | perpendicular to upwards |
| Leaf stem color | Yellow-Green Group 146D | Yellow-Green Group 146D |
| Trifoliate leaf blade Length (cm) | 12.9 | 13.0 |
| Trifoliate leaf blade Width (cm) | 16.5 | 16.3 |
| Petiole length (cm) | | |
| Low fertility conditions | 13.0 | 12.2 |
| High fertility conditions | 18.2 | 16.3 |
| Petiolule length (mm) | 5.0 | 3.6 |
| Petiolule diameter (mm) | 1.7 | 1.5 |
| Stolon diameter (mm) | 2.9 | 2.8 |
| Stolon Color | Red Group 42C | Yellow-Green Group 152B |
| Stipule Coloration | Red Group 46A | Yellow-Green Group 144B |

Flower and Fruit Characteristics

The length of bloom for 'Wendy' is about three weeks when grown in Kentville, Nova Scotia, Canada in a matted row cultural system. Flowering for 'Wendy' and 'Evangeline' typically begins on May 21 and ends on June 11. As shown in Table 2, the flower truss of 'Wendy' averages 3.7 cm longer than for 'Evangeline' but flowers of both varieties open even with the leaf canopy or slightly below. 'Wendy' flower trusses produce slightly more flowers than 'Evangeline'. Flowers of 'Wendy' and 'Evangeline' are white which is not included on The Royal Horticultural Society Colour Chart. The anther color is Yellow-Orange Group 17 A. Secondary flowers of 'Wendy' usually have 5 petals, occasionally 6, 'Wendy' flowers are smaller than those of 'Evangeline'. Petals of both varieties are longer than wide. Petals of 'Wendy' generally touch while those of 'Evangeline' are spaced. Trusses of 'Wendy' are semi-erect at first picking while those of 'Evangeline' are erect. The outer calyx of 'Wendy' is larger than for 'Evangeline' but the inner calyx is about the same size. The position of the calyx is even with the top of the fruit for 'Wendy' but raised for 'Evangeline'. The color of the inner calyx of 'Wendy' is Green Group 141C and the outer calyx is darker green Green Group 143A. Both inner and outer calyx of 'Evangeline' are Green Group 141C. The calyx is easily separated from the fruit for both varieties. The secondary fruit of 'Wendy' are larger than for 'Evangeline' and conic in shape while the fruit of 'Evangeline' are conic to long conic, and generally longer than wide. The seeds of 'Wendy' are even with the surface of the fruit or slightly indented whereas 'Evangeline' seeds are more deeply indented. The flesh of both varieties is considered firm. The fruit color of 'Wendy' and 'Evangeline' is the lighter Red Group 45A when the fully red stage is reached to the darker Red Group 46A when the fruit is more mature. The pith of 'Wendy' is similar to or a bit darker than the pith of 'Evangeline' but the cortex colors are very similar, recorded at 45A or 46B for 'Wendy' and 45A or 45B for 'Evangeline' depending on their ripeness. The pith of 'Wendy' occupies one-half of the width of the berry and is white at the proximal end of the berry changing to the same color red as the cortex at the distal end. The berry vasculature is white. The achenes of 'Wendy' are Green-Yellow Group 1A but darken to Orange-Red Group 34 A on the side of the fruit when exposed to sunlight. Measurements for the reproductive organs were made on secondary flowers within two days of their opening. Both 'Wendy' and 'Evangeline' have yellow anthers (Yellow Group 17A), yellow-green filaments (Yellow-green group 145B), and the central part of the flower, the pistols, is Yellow-green group 150B. The diameter of the pistol-covered receptacle is 5.1 mm for 'Wendy' and 5.2 mm for 'Evangeline'. The stamen length is 3.2 mm for 'Wendy' and 3.5 mm for 'Evangeline'. The anther length is 1.8 mm for 'Wendy' and 1.5 mm for 'Evangeline'.

TABLE 2

Flower and fruit characteristics for 'Wendy' and 'Evangeline'

| Character | Cultivar 'Wendy' | Cultivar 'Evangeline' |
|---|---|---|
| Flower Position (relative to leaf canopy) | even or slightly beneath | even or slightly beneath |
| Flower truss length | medium 26.8 | short-medium 23.1 cm |
| Number of flowers/truss | 9.0 | 8.3 |
| Number of petals | 5.2 | 5.0 |
| Flower size (mm diameter | 32.4 | 35.8 |
| Petal length (mm) | 13.7 | 15.3 |
| Petal width (mm) | 12.2 | 12.6 |
| Petal spacing | touching | spaced |
| Calyx size | | |
| Inner calyx (mm diam.) | 32.3 | 32.1 |
| Outer calyx (min diam.) | 36.8 | 33.4 |
| Calyx position | even | raised |
| Adherence of the calyx | weak | weak |
| Fruit size and shape | | |
| Length (mm) | 32.2 | 31.8 |
| Width (mm) | 32.8 | 30.3 |
| Length/width ratio | 0.98 | 1.05 |
| Subjective fruit shape | conic | conic to long-conic |
| Achene position | even to Slightly indented | indent |
| Fruit firmness | firm | firm |
| Fruit firmness (Newtons) | 4.9 | 4.5 |
| Color | | |
| Calyx | Green Group 141C to 143A | Green Group near 141C |

TABLE 2-continued

Flower and fruit characteristics for 'Wendy' and 'Evangeline'

| Character | Cultivar 'Wendy' | Cultivar 'Evangeline' |
|---|---|---|
| Fruit exterior | Red Group 45A To 46A | Red Group 45A to 46A |
| Fruit interior | Red Group | Red Group |
| Pith | 45A to 46B | 45A |
| Cortex | 45A to 46B | 45A to 45B |

Disease Resistance

'Wendy' and 'Evangeline' are susceptible to red stele root rot (*Phytophthora fragariae*). 'Evangeline' is resistant to powdery mildew (*Sphaerotheca macularis*) while 'Wendy' is moderately resistant. 'Wendy' and 'Evangeline' are moderately resistant to fruit rot (*Botrytis cinerea*).

Production Characteristics

'Wendy' has been widely tested for several years and in replicated trials planted in 2003 and harvested in 2004. 'Wendy' has consistently produce higher yields than 'Evangeline', as shown in Table 3. The percent marketability of both varieties is similar, indicating the lack of problems with pollination or fruit diseases. The fruit of 'Wendy' are much larger (by weight) than 'Evangeline'. The mean harvest date for 'Wendy' is one day later than for 'Evangeline'. Subjectively, the flavor of the fruit of 'Wendy' is rated very good to excellent when fully ripe. Fruit of 'Wendy' when stored at 5° C. will remain in marketable condition for 5 days compared to 4 days for 'Evangeline'. The market use of 'Wendy' is for fresh markets in Eastern Canada and northeastern and mid-western United States.

TABLE 3

Performance of 'Wendy' and 'Evangeline' for 2004 at Kentville, N.S. and Bouctouche, N.B. Plants were grown in matted rows and three blocks of 3 m long rows were harvested at each site.

| | Total yield (t/ha) | % yield marketable | Size (g/fruit) | Mean day of harvest |
|---|---|---|---|---|
| 2004 (Kentville) | | | | |
| 'Wendy' | 21.1 | 90.3 | 17.1 | July 10 |
| 'Evangeline' | 10.8 | 88.5 | 11.1 | July 9 |
| 2004 (Bouctouche) | | | | |
| 'Wendy' | 8.3 | 85.0 | 13.3 | July 13 |
| 'Evangeline' | 5.8 | 90.1 | 9.9 | July 12 |

What is claimed:

1. The new and distinct variety of strawberry plant named 'Wendy' as described and illustrated herein.

* * * * *